United States Patent [19]

Shimizu et al.

[11] Patent Number: 5,275,602
[45] Date of Patent: Jan. 4, 1994

[54] BONE-JOINING ARTICLES

[75] Inventors: Yoshihiko Shimizu, 39-676, Ogurayama, Kohata, Uji-shi, Kyoto-fu; Tatsuo Nakamura; Teruo Matsui, both of Kyoto; Nobuya Takahashi, Kobe; Takeshi Shimamoto, Fukuchiyama, all of Japan

[73] Assignees: Gunze Limited; Yoshihiko Shimizu, both of Kyoto, Japan

[21] Appl. No.: 961,193

[22] Filed: Oct. 14, 1992

Related U.S. Application Data

[63] Continuation of Ser. No. 707,889, Jun. 3, 1991, abandoned.

[51] Int. Cl.5 .............................................. A61B 17/00
[52] U.S. Cl. .......................................... 606/72; 606/77
[58] Field of Search .................... 606/60, 72, 74, 77, 606/78, 69

[56] References Cited

U.S. PATENT DOCUMENTS 1,156,440 10/1915 Smith ................................. 606/74
3,710,789 1/1973 Ersek ................................. 606/60
4,905,680 3/1990 Tunc ................................. 606/77 X
4,968,317 11/1990 Tormala et al. ...................... 606/77
5,007,939 4/1991 Delcommune et al. ............. 606/77 X

FOREIGN PATENT DOCUMENTS 295041 12/1988 European Pat. Off. .............. 606/60

OTHER PUBLICATIONS

Article by Nicholas Senn, M.D., Transcript of speech to ASA, May 30, 1893.

Primary Examiner—Robert A. Hafer
Assistant Examiner—Sam Rimell
Attorney, Agent, or Firm—Armstrong, Westerman, Hattori, McLeland & Naughton

[57] ABSTRACT

The invention provides an article for joining the pieces of a fractured bone, characterized in that the article is composed of a high-molecular weight material which is absorbable in the living body and that the article is in the form of a tubular body having a hollow interior and a cutout extending over the entire length of the tubular body in the longitudinal direction thereof.

2 Claims, 1 Drawing Sheet

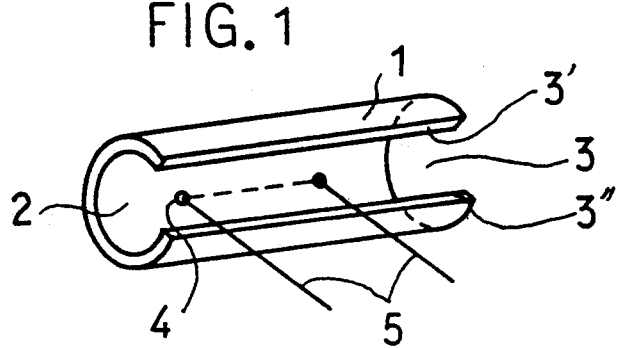
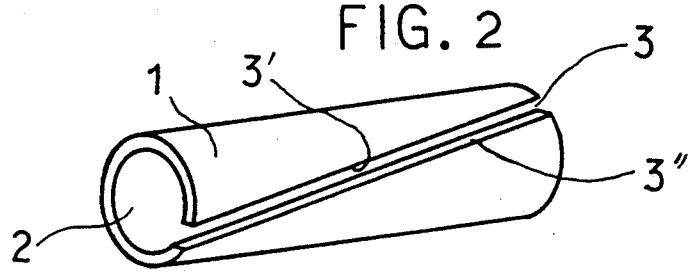
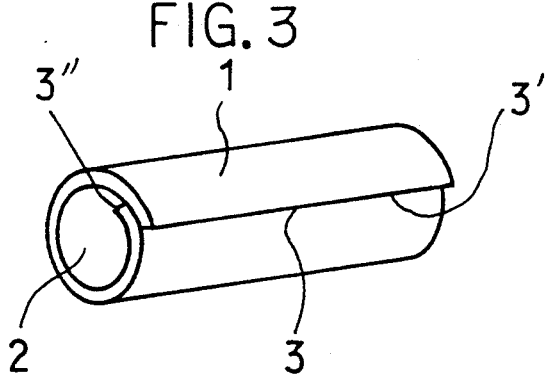
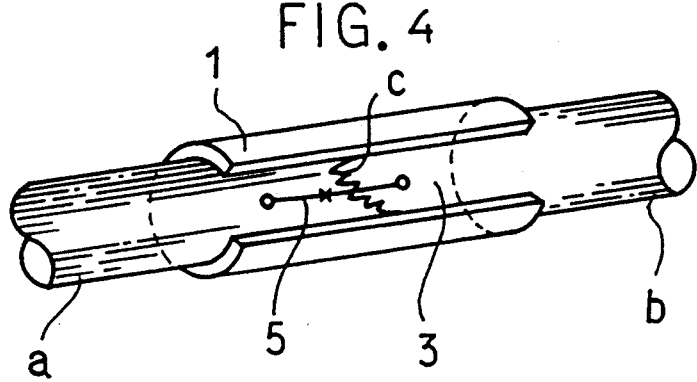

BONE-JOINING ARTICLES

This application is a continuation of application Ser. No. 707,889 filed Jun. 3, 1991, now abandoned.

BACKGROUND

The present invention relates to an article for use in joining the pieces of a broken bone, and more particularly to an article useful in joining the pieces of a broken bone, the article being composed of a material which is absorbable in the living body.

PRIOR ART

Since this type of bone-joining article is required to have a considerable strength, metals, alumina ceramics and like inorganic materials have been conventionally used to produce the article. These articles, however, have drawbacks. For example, when left in the living body after healing, the articles are so rigid as to reduce the strength of recovered bone, and re-operation is necessitated for removal of the article from the cured bone.

Bone-joining articles made of in vivo absorbable materials have been proposed. Yet, in vivo absorbable materials per se have the defect of unsatisfactory mechanical strength. Conventional bone-joining articles of in vivo absorbable materials have been produced in the form of a pin, plate, screw or the like. The articles in such form remain unsatisfactory in strength. Further, these articles require a high skill and take a considerable time in mending a complicated fracture caused due to, e.g., traffic accidents. Moreover, these articles are difficult to securely fix to the bone, and the attached articles are likely to be displaced or removed by an external force.

It is an object of the present invention to provide a bone-joining article which is made of an in vivo absorbable material and which has a high mechanical strength.

It is another object of the invention is to provide a bone-joining article which is made of an in vivo absorbable material and which is easily applicable to a broken bone, including a complicated fracture, in a short time.

These and other objects of the invention will become more apparent from the following description.

According to the invention, there is provided an article for joining the pieces of a broken bone, characterized in that the article is composed of a high-molecular weight material which is absorbable in the living body and that the article is in the form of a tubular body having a hollow interior and a cutout extending over the entire length of the tubular body in the longitudinal direction thereof.

Our research has revealed the following. Since the bone-joining article made of an in vivo absorbable material according to the invention is in the form of a hollow cylinder, the article is remarkably improved in mechanical strength compared with conventional bone-joining articles in the form of a pin, plate or the like. Because the bone-joining article of the invention has a cutout formed over the entire length of the tubular body in the longitudinal direction thereof, the broken bone pieces to be joined can be easily ensheathed tightly in the hollow interior due to the elasticity of in vivo absorbable high-molecular weight material by pushing the cutout open and inserting the pieces into the interior utilizing the flexibility of absorbable material. Therefore, even a complicated fracture can be easily mended without notably high skills in a short time, and the bone pieces can be stably held in position without displacement or removal by an external force. In addition, the bone-joining article of the invention which is made of in vivo absorbable material need not be removed from the healed bone. The bone-joining article of the invention with these features can be suitably used to mend not only a complicated fracture caused due to traffic accidents or the like but also bones surgically cut.

In vivo absorbable high-molecular weight materials constituting the bone-joining article of the invention include, for example, a wide variety of polymeric materials which have been conventionally used as materials for medical articles and which are hydrolyzed in and absorbed by the living body. Specific examples of such in vivo absorbable high-molecular weight materials are polylactides, polyglycolides, lactide-glycolide copolymers, polyparadioxanones, polycaprolactams, collagens, etc. Useful in vivo absorbable high-molecular weight materials may have a wide range of molecular weight, usually not less than 30,000, preferably not less than 100,000, most preferably about 100,000 to about 300,000. Suitable among them are polylactides (polymer of d-, dl- or l-lactide) and lactide-glycolide copolymers which have a molecular weight in the above range. The bone-joining articles of such polymeric materials can retain the strength for an extended period of time, i.e. several months or longer, after application. The foregoing polymeric materials can be further improved in strength by stretching or by being mixed with other substances into a composite material.

The present invention will be described below in more detail with reference to the accompanying drawings showing embodiments of the invention in which:

FIGS. 1, 2 and 3 are perspective views schematically showing embodiments of bone-joining articles of the invention; and FIG. 4 is a perspective view schematically showing the bone-joining article of the invention as applied to a bone fracture.

In the drawings, indicated at 1 is a tubular body; at 2, a hollow interior; and at 3, a cutout extending in the longitudinal direction of the tubular body. FIG. 1 shows an embodiment of the invention in which the cutout 3 extends in parallel over the entire length of the tubular body 1 in the longitudinal direction thereof and is provided with the ends 3', 3" of the cutout 3 spaced away from each other without joining. FIG. 2 shows another embodiment of the invention in which the cutout 3 extends obliquely over the entire length of the tubular body 1 in the longitudinal direction thereof and is formed with the ends 3', 3" of the cutout 3 as opposed to each other with a slight spacing therebetween. FIG. 3 illustrates a further embodiment of the invention in which the cutout 3 extends in parallel over the entire length of the tubular body 1 in the longitudinal direction thereof, and is provided with the ends 3', 3" of the cutout 3 overlapping each other. Through holes 4 are formed in the tubular body 1 as shown in FIG. 1 for insertion of sutures 5 for fastening the bone pieces to be joined together.

The tubular body 1 may have either a circular or an elliptical cross section according to the shape of the broken bone to be covered therewith. The wall thickness of the tubular body 1 is selected depending on the time period to be taken for healing the broken bone. For example, when used in mending a broken bone which will take a long time in recovery, the tubular body 1 is one having a wall thickness sufficient to retain the required strength during the healing period. For use in joining the pieces of a broken bone to be healed in a short time, the tubular body 1 may have a correspondingly thin wall thickness. Therefore the wall thickness of the tubular body 1 is not specifically limited and can be selected over a wide range. A typical wall thickness of the body is in the range of about 0.5 to about 2.5 mm, preferably about 1 to about 2 mm. The diameter of the hollow interior 2 can be varied over a wide range according to the thickness of the bone to be enclosed therewith. For example, adults' ribs may be mended with preferably a tubular body of elliptical cross section in conformity of the bone which body has a hollow interior about 10 to about 20 mm in the direction of longer diameter and about 5 to about 10 mm in the direction of shorter diameter. In mending infants' or adults' bonelets or like thin bones, a tubular body of circular or elliptical cross section to be used is one having a hollow interior about 5 to about 10 mm in the direction of longer diameter and about 3 to about 5 mm in the direction of shorter diameter. In mending adults' humeri, thigh bones or like thick bones, a tubular body of circular or elliptical cross section to be selected has a hollow interior about 30 to about 40 mm in the direction of longer diameter and about 20 to about 30 mm in the direction of shorter diameter.

The length of the tubular body 1 can be suitably selected according to the conditions of bone fracture and may be one which is sufficient to cover the broken portion and the surrounding portion and to securely hold the broken bone in place. The length of the body 1 is usually in the range of about 10 mm to about 50 mm.

The cutout 3 of the tubular body 1 is provided over the overall length of the tubular body 1 in the longitudinal direction thereof. In mending a bone fracture with the bone-joining article of the invention, the cutout 3 is pushed open due to the flexibility of the body 1 and bone pieces (a) and (b) temporarily engaged with each other at a fractured part (c) are inserted into the hollow interior 2 to ensheathe the fractured part (c) tightly in the body 1 utilizing the elasticity thereof. The cutout 3 is formed over the entire length of the body 1 in the longitudinal direction thereof and may be provided in parallel or obliquely in said direction. The ends 3', 3" of the cutout 3 may be overlapped or spaced away in opposition. The most desirable is the cutout 3 depicted in FIG. 1 which extends in parallel over the entire length of the body 1 in the longitudinal direction thereof with the ends 3', 3" spaced away. The spacing of the cutout 3 shown in FIG. 1 is variable with the diameters of the broken bone and the hollow interior 2, and is in the range of about 2 to about 20 mm, preferably about 5 to about 10 mm.

The bone-joining article of the invention can be produced, for example, by the following methods. A sheet of in vivo absorbable material having a thickness of about 0.5 to about 2.5 mm may be rolled up such that the ends 3', 3" are overlapped or brought to an opposite position with spacing therebetween to form a tubular body 1 with a cutout 3. Alternatively a rod-like material is bored in its longitudinal center to give a tubular body 1 with a cutout 3. Optionally a material may be extruded into a molded tubular body 1 in which a cutout 3 is formed simultaneously or by further processing.

The bone-joining article of the invention can be applied to a broken bone, for example as shown in FIG. 4. As depicted in FIG. 4, the bone pieces (a) and (b) in a complicated fracture are temporarily engaged with each other at the fractured part (c), and the cutout 3 is pushed open by virtue of the flexibility of the body 1, whereupon the bone pieces (a) and (b) engaged at the part (c) are brought into the hollow interior 2 to encase the part (c) tightly with the body 1 utilizing the elasticity thereof. Then the bone pieces (a) and (b) are bored at the locations corresponding to the through holes 4, and then a suture 5 formed from the same in vivo absorbable material as the bone-joining article of the invention is passed through the resulting holes and is bound for fastening. To cover the broken bone with the tubular body 1, the cutout 3 is usually pushed open in the direction of diameter. Then the bone covered with the body 1 is kept in tight contact with the internal wall of hollow interior 2 due to the elasticity of the tubular body material. The most preferred method of applying the article of the invention comprises stretching the tubular body 1 of the invention in longitudinal and lateral directions before application to obtain a body of larger diameter than the broken bone, applying the body 1 to the bone and heating the body 1 to shrink it, whereby the broken bone is held in fixed position with the shrunk body.

In the embodiment shown in FIG. 1, the cutout 3 is provided with the ends 3', 3" as spaced from each other in parallel in the longitudinal direction of the tubular body 1. In this embodiment, the broken bone is preferably enclosed with the tubular body 1 so formed that the cutout 3 of the body 1 applied to the bone has an opening between the ends 3' and 3" by a distance of approximately ⅓ the entire circumference of the body 1 around the bone. The tubular body 1 so formed can be caused to easily encase the bone tightly without interrupting the blood flow. The bone-joining article of the invention can be applied to the broken bone not only by pushing open the cutout 3 to encase the bone, but also by inserting one of the bone pieces through one end of the tubular body 1 and the other bone piece through the other end thereof after which the bone pieces are joined within the body 1. The latter method is suitable for joining the bone pieces with a tubular body of such large wall thickness as to make it difficult to open the cutout 3.

After enclosing the bone with the tubular body 1, a suture of in vivo absorbable material may be passed into the through holes in the above manner and bound to hold the bone in position. Alternatively a suture of metal wire may be used in place of the suture of in vivo absorbable material. Optionally a suture of metal wire or in vivo absorbable material may be wound on the entire circumference of the tubular body 1 to immobilize the bone. It is also possible to fix the bone pieces with a bolt, a nut or the like made of in vivo absorbable material.

In this way, the treatment of broken bone can be completed, and thereafter the joined bone pieces are left without attention until the fracture is healed. During the healing period, the tubular body 1 is hydrolyzed and absorbed in the living body into extinction, namely eliminating the need to remove the body 1 from the healed bone.

What we claim is:

1. A therapeutic method for joining pieces of a broken bone, comprising the steps of:
    supplying a high-molecular weight material which is absorbable in the living body;
    forming said material into the form of a tubular body having an elasticity, a hollow interior, and a cutout extending over the entire length of the tubular body in a longitudinal direction thereof;
stretching the tubular body to obtain a body of larger diameter than the broken bone;
passing said broken bone into said hollow interior of said tubular body; and
heating said tubular body to shrink, such that said tubular body surrounds said broken bone and clamps said pieces of broken bone in place due to a clamping force of the shrunk tubular body.

2. The method of claim 1, wherein in said step of passing said broken bone into said hollow interior, with the aid of said elasticity of said tubular body, said cutout is opened and said broken bone is passed therethrough to said hollow interior.

* * * * *